United States Patent
Hansen (10) Patent No.: US 9,681,692 B2
(45) Date of Patent: Jun. 20, 2017

(54) POST-OPERATIVE STERNUM AND BREAST DEVICE

(71) Applicant: Doris Hjorth Hansen, Chiaverano (IT)

(72) Inventor: Doris Hjorth Hansen, Chiaverano (IT)

(73) Assignee: QUALITEAM S.R.L., Chiaverano (IT)

( * ) Notice: Subject to any disclaimer, the term of this patent is extended or adjusted under 35 U.S.C. 154(b) by 16 days.

(21) Appl. No.: 14/868,944

(22) Filed: Sep. 29, 2015

(65) Prior Publication Data
US 2016/0374406 A1   Dec. 29, 2016

(30) Foreign Application Priority Data
Jun. 26, 2015  (EP) .................................... 15425049

(51) Int. Cl.
| A41C 3/00 | (2006.01) |
| A61F 5/03 | (2006.01) |
| A61F 13/14 | (2006.01) |
| A41C 3/02 | (2006.01) |

(52) U.S. Cl.
CPC .......... *A41C 3/0064* (2013.01); *A41C 3/0028* (2013.01); *A41C 3/02* (2013.01); *A61F 5/03* (2013.01); *A61F 13/145* (2013.01)

(58) Field of Classification Search
CPC ....... A41C 3/0064; A41C 3/005; A41C 3/148; A61F 13/14
USPC .. 450/58, 78, 79, 82, 83, 62–64, 23, 24, 59, 450/60; 2/19, 61
See application file for complete search history.

(56) References Cited

U.S. PATENT DOCUMENTS

| 244,776 A | 7/1881 | Wales |
| 693,115 A | 2/1902 | Cozzens |
| 1,189,589 A | 7/1916 | Lawrence |

(Continued)

FOREIGN PATENT DOCUMENTS

| DE | 20 2006 008380 U1 | 8/2006 |
| EP | 0 260 351 A1 | 3/1988 |

(Continued)

OTHER PUBLICATIONS

May 22, 2003 Search Report for Great Britain Application No. GB 0227838.0 (1 page).

(Continued)

*Primary Examiner* — Gloria Hale
(74) *Attorney, Agent, or Firm* — Popovich, Wiles & O'Connell, P.A.

(57) ABSTRACT

A support device for providing external support for a patient's chest and breast after the patient has undergone a surgical procedure in the thoracic region. The support device includes a chest band and first and second elongate under-bust/shoulder bands. Each of the under-bust/shoulder bands includes an under-bust portion and a shoulder strap portion. The support device includes first and second connectors attached to the shoulder strap portions of the second and first elongate bands, respectively. A lower portion of a first breast encapsulating unit is attached to the under-bust portion of the first under-bust/shoulder band and an upper portion is attached to the first connector. A lower portion of a second breast encapsulating unit is attached to the under-bust portion of the second under-bust/shoulder band and an upper portion is attached to the second connector.

12 Claims, 8 Drawing Sheets

(56) References Cited

U.S. PATENT DOCUMENTS

| | | | |
|---|---|---|---|
| 2,553,225 A * | 5/1951 | Weaver | A41C 3/0021 |
| | | | 450/59 |
| 2,723,396 A | 11/1955 | Stack | |
| 2,725,563 A | 12/1955 | Rich | |
| 2,800,902 A | 7/1957 | Wiltrout | |
| 2,870,768 A | 1/1959 | Robinson | |
| 3,194,234 A | 12/1963 | Duckman et al. | |
| 3,400,710 A | 9/1968 | Goldstein | |
| 3,439,682 A | 4/1969 | Defru | |
| 3,554,190 A | 1/1971 | Kaplan | |
| 3,561,442 A | 2/1971 | Goswitz | |
| 3,623,487 A | 11/1971 | Chiu | |
| 3,710,800 A | 1/1973 | Carey | |
| 3,968,803 A | 7/1976 | Hyman | |
| 3,970,079 A | 7/1976 | Gaylord, Jr. | |
| 4,022,197 A | 5/1977 | Castiglia | |
| 4,024,876 A | 5/1977 | Penrock | |
| 4,081,150 A | 3/1978 | Tyson | |
| 4,207,885 A | 6/1980 | Hampton et al. | |
| 4,254,777 A | 3/1981 | Johnston | |
| 4,308,629 A | 1/1982 | Freemon | |
| 4,396,013 A | 8/1983 | Hasslinger | |
| D273,331 S | 4/1984 | Gruber | |
| 4,630,610 A | 12/1986 | Fletcher | |
| 4,802,469 A | 2/1989 | Gollestani | |
| 4,804,351 A | 2/1989 | Raml et al. | |
| 4,901,373 A | 2/1990 | Broersma | |
| 4,957,466 A | 9/1990 | Hopps | |
| 4,960,112 A | 10/1990 | Anderegg | |
| 5,011,452 A | 4/1991 | Kelly | |
| 5,037,348 A | 8/1991 | Farino | |
| 5,040,526 A | 8/1991 | Erickson | |
| 5,098,331 A | 3/1992 | Corrado | |
| 5,123,121 A | 6/1992 | Broersma | |
| 5,152,741 A | 10/1992 | Farnio | |
| 5,221,227 A | 6/1993 | Michels | |
| 5,242,237 A | 9/1993 | Wagner | |
| 5,265,910 A | 11/1993 | Barr et al. | |
| D349,767 S | 8/1994 | Courtet | |
| 5,411,461 A | 5/1995 | Thomascik | |
| 5,421,809 A | 6/1995 | Rise | |
| 5,423,711 A | 6/1995 | Dorland | |
| 5,503,620 A | 4/1996 | Danzger | |
| 5,527,270 A | 6/1996 | Chase et al. | |
| 5,538,502 A | 7/1996 | Johnstone | |
| 5,634,439 A | 6/1997 | O'Brien | |
| 5,664,257 A | 9/1997 | Hall | |
| 5,790,983 A | 8/1998 | Rosch et al. | |
| 5,797,786 A | 8/1998 | Smith et al. | |
| 5,839,942 A | 11/1998 | Miller | |
| 5,843,008 A | 12/1998 | Gerhard | |
| 5,954,681 A | 9/1999 | Brooks | |
| D416,651 S | 11/1999 | Lanoue | |
| 6,048,253 A | 4/2000 | Larsen | |
| 6,068,606 A | 5/2000 | Castel et al. | |
| 6,135,975 A | 10/2000 | Johnstone | |
| 6,165,045 A | 12/2000 | Miller et al. | |
| 6,240,564 B1 | 6/2001 | Te Kanawa | |
| 6,280,287 B1 | 8/2001 | Keith et al. | |
| 6,296,618 B1 | 10/2001 | Gaber | |
| 6,309,369 B1 | 10/2001 | Lebovic | |
| 6,394,879 B1 | 5/2002 | Paige | |
| 6,431,947 B1 | 8/2002 | Henz | |
| 6,460,747 B1 | 10/2002 | Tuerschmann et al. | |
| 6,464,717 B1 | 10/2002 | Smith et al. | |
| 6,516,804 B1 | 2/2003 | Hoffman | |
| 6,550,286 B2 | 4/2003 | Querquant | |
| D499,806 S | 12/2004 | Machin et al. | |
| 6,921,375 B2 | 7/2005 | Kihara | |
| D517,215 S | 3/2006 | Cheney | |
| 7,056,187 B2 | 6/2006 | Cassity | |
| 7,144,294 B2 | 12/2006 | Bell et al. | |
| 7,160,262 B2 | 1/2007 | Wicks | |
| 7,347,695 B2 | 3/2008 | Ware et al. | |
| 7,435,155 B2 | 10/2008 | Reinisch et al. | |
| 7,530,333 B2 | 5/2009 | Sumner et al. | |
| D595,859 S | 7/2009 | Young | |
| 7,568,967 B2 | 8/2009 | Smith | |
| 7,666,058 B2 * | 2/2010 | Smith | A41C 3/0064 |
| | | | 450/20 |
| 7,806,748 B2 | 10/2010 | Richardson | |
| D628,300 S | 11/2010 | Caden | |
| 7,850,508 B2 * | 12/2010 | Pitarelli | A41C 3/0064 |
| | | | 450/85 |
| 8,016,640 B2 | 9/2011 | Morgan | |
| 8,123,588 B2 | 2/2012 | Tyrer | |
| D657,063 S | 4/2012 | Chiang | |
| D658,350 S | 5/2012 | Goodman | |
| D661,402 S | 6/2012 | Chen et al. | |
| 2001/0034498 A1 | 10/2001 | Heyman et al. | |
| 2003/0092355 A1 | 5/2003 | Rabinowicz et al. | |
| 2006/0047236 A1 | 3/2006 | Hansen | |
| 2006/0135898 A1 | 6/2006 | Richardson | |
| 2007/0179421 A1 | 8/2007 | Farrow | |
| 2008/0251087 A1 | 10/2008 | Richardson | |
| 2010/0049109 A1 | 2/2010 | Stewart, III | |
| 2011/0004970 A1 | 1/2011 | Okamoto | |
| 2011/0112453 A1 | 5/2011 | Petiot et al. | |
| 2011/0251543 A1 | 10/2011 | Hansen | |
| 2012/0271212 A1 | 10/2012 | Grisham-Algots | |
| 2012/0310127 A1 | 12/2012 | Zacharopoulos | |
| 2013/0065486 A1 * | 3/2013 | Hansen | A41C 3/0064 |
| | | | 450/59 |
| 2013/0157527 A1 * | 6/2013 | Raynes | B63H 21/17 |
| | | | 440/6 |
| 2014/0196189 A1 | 7/2014 | Lee et al. | |
| 2015/0099420 A1 | 4/2015 | Reinhard | |

FOREIGN PATENT DOCUMENTS

| | | |
|---|---|---|
| EP | 0 368 583 A1 | 5/1990 |
| GB | 1 054 741 A | 1/1967 |
| WO | WO 93/06936 A1 | 4/1993 |
| WO | WO 99/65428 A1 | 12/1999 |
| WO | WO 2004/049841 A2 | 6/2004 |
| WO | WO 2006/092819 A1 | 9/2006 |
| WO | WO 2010/025186 A1 | 3/2010 |

OTHER PUBLICATIONS

Jun. 14, 2004 Search Report for International Application No. PCT/IB03/06395 (5 pages).
QualiBreath brochure 2011 (2 pages).
Abstract for DE 20 2006 008380 U1 (1 page).
Nov. 13, 2015 EPO Communication for European Application No. 15425049.2 (7 pages).
Cheifetz et al., The Effect of Abdominal Support on Functional Outcomes in Patients Following Major Abdominal Surgery. Physiotherapy Canada, vol. 62, No. 3. p. 242-253.
Feb. 3, 2014 European Search Report for EP Application No. 13425134.7 (6 pages).
QualiBelly Advanced brochure 2011 (2 pages).
QualiBelly brochure 2010 (2 pages).
QualiBra Advanced Hospital Brochure 2014 (2 pages).

* cited by examiner

POST-OPERATIVE STERNUM AND BREAST DEVICE

FIELD OF THE INVENTION

The present invention relates to providing external support to female patient's chest and to support their breasts after they have undergone a surgical procedure in the thoracic region. In particular, the present invention relates to a sternum and breast device that provides external, lateral support to the two sternum halves, and provides individual support and positioning of the breasts after female patients have undergone surgeries requiring opening of the sternum bone, referred to as a sternotomy.

BACKGROUND OF THE INVENTION

The soft tissue of a sternal wound takes about 4-5 weeks to heal and the sternum bone between 6-8 weeks for a proper healing. In this postoperative period there are only the internal stainless steel wires, bands, plates or other devices to keep the thorax integrity intact. If the sternum bone closure is not stable, the soft tissue of the sternum wound may not be strong enough alone to support the sternum in case of excessive strain as during coughing, sneezing, exercises, or sudden movements involving the patient's upper extremities.

Effective methods to prevent postoperative complications in the healing period are crucial to decrease the costs of health care. The overall incidence of deep sternal wound infections (DSWI) after sternotomy procedures ranges from 0.3% to 5% during hospitalization with a morbidity between 14% and 47% and increases the length of hospital stay with additional 4 to 8 weeks. The incidence of DSWI increases to 7.3% at 90 days after discharge. Superficial sternal wound infections (SWI) are reported to be from 0.5% to 8% in the hospital, and increases to 9% after 90 days. Twenty five (25) % of SWI and more than 33% of DSWI cases are diagnosed between 30 and 90 days after surgery, while as many as 50% of SWI and 80% of DSWI are diagnosed at 90 days post-discharge. Postoperative pulmonary complications (PPC) after sternotomy are complex and not well understood. The frequency is reported to be from 7% to 79%. Furthermore between 11% and 56% of sternotomy patients suffer from persistent postoperative pain, a fact that is largely underestimated.

The health care system has additional costs of about $45,000 per patient with DSWI, or almost 3 times the cost of a normal procedure without complications ($18,000) [22]. Postoperative pulmonary complications and persistent pain add costs per patient of $28,000 and $6,000 respectively, however, since the rate of incidence is much higher, these complications represent a significantly higher economic burden on the health care system.

The major risk factors for sternal wound infection are obesity, breast size, diabetes, osteoporosis, chronic cough, tobacco use, chronic obstructive pulmonary disease (COPD), immuno-suppression, and CABG with use of the Internal Mammary Arteries (IMA). Women who need large bra cups have a 38.5% higher risk for deep sternal wound infection compared with women who need small bra cups. Women who need medium bra cups have a 12.3% higher risk for sternal wound infection.

Research reported in literature demonstrates the serious need for effective prevention of postoperative complications after sternotomy procedures to decrease health care costs and to improve patient's postoperative recovery experience.

Since improved surgical techniques have not decreased the incidence of complications over the last decades, there is an increased need for postoperative devices that can complement the internal sternal closure through a lateral sternum reinforcement from the outside, assist patients to better manage their breathing and pain, and provide increased support when they cough, sneeze, strain or perform exercises in the rehabilitation period.

Following thoracic surgeries and in particular surgeries requiring access through the sternum bone, women in general, fuller-sized women in particular, and obese patients more in particular, encounter a significantly higher risk for postoperative complications such as sternal and pulmonary infections, as well as additional pain and wound healing complications caused by strain on the sternum bone from the weight of the breast tissue, and from the additional internal pressure caused by coughing, sneezing and straining e.g. during bowel movements and/or excessive and wrong use of upper extremities too early after surgery. The mass of breast tissue causes the gravity force to pull the tissue downwards when a person is in the standing or sitting position, and to the lateral sides when a person is in the horizontal position or leaning backwards. Such pulling force causes significant stress on a fresh sternum wound and on the two halves of the sternum bone that after surgery are only held together on the inside by surgical stainless steel wires, bands, plates or similar devices. The weight pull from the breast tissue will draw the two wound edges away from each other and may cause the skin sutures to cut through the skin and wound edges, breaking the wound open. Such open or partially open wound will increase the risk of wound infections, wound deformations, deeper wound rupture and cause additional pain. In an even worse scenario, the pulling force from heavy breast tissue will cause the sternum stainless steel wires, bands or plates to cut into or through the sternum bone. This will cause pain, sternum dehiscence, and significantly increase the risk for deep sternal wound infections, all which are very severe postoperative complications with high mortality rates and very high costs to cure.

Therefore the sternum must be supported laterally from the external side to complement and support the internal surgical closure, and the breast tissue, in particular fuller-sized breast tissue, must be supported and positioned to prevent gravity pulling forces in any direction on a wound in the chest and in particular a sternal wound which is placed centrally between the breasts. Furthermore a continuous external lateral support on the sternum bone is particularly important when the patient coughs, sneezes or when straining such as during bowel movements. These actions significantly increase the internal thoracic pressure up to as high as 300 mmHg. Such sudden increased thoracic pressure will cause additional stress on the sternum bone closure from the inside and increase the risk for rupture of the sternum closure, particularly if the sternum is unsupported from the external side. Therefore it is important not only to have a constant external chest support, but in addition to have means available to increase the external lateral support on the sternum to counteract such increased internal thoracic pressure and prevent postoperative complications.

Just as the pulling force on the wound caused by heavy breast tissue must be controlled and counteracted, the wound, and in particular a sternum wound must be protected from being squeezed from the sides by breast tissue. Such squeezing pressure on a wound will encapsulate the wound and generate heat and moisture, which can cause bacterial growth and result in severe wound infections. Therefore the breast tissue must gently be kept away from the wound, and particularly from a sternum wound, without introducing a pulling force on the wound, to prevent heat and moisture production with potential accompanying wound complications.

Additionally, squeezing a wound, and in particular a sternum wound, disturbs the natural healing process, and may result in deformation of the wound, which leaves an esthetically, unattractive scar in a highly visible place on a patient's chest. This may be a psychological problem for the patient postoperatively, and in particular, it may be a psychological problem for women postoperatively.

Inspection and care of a fresh surgical wound requires access by opening of the dressings, bands, brassieres and other devices which may cover the wound after surgery. Wound inspection and care represent particularly a problem in obese patients and fuller sized women, since the support of breast tissue is interrupted during such wound exposure. The gravity force will pull, cause pain and stress on the wound during care, whereby the risk of postoperative complications may increase. Therefore support of the breasts must be maintained at all times including when wound inspection and care is taking place to prevent such complications and the related increased costs of cure.

In addition, wound care of sternotomy patients with exposure of breasts may represent an issue for women of different ethnical origins. Therefore it is desirable particularly for this group of patients that the breast tissue is covered at all times including during wound care.

Accordingly there is a need for a postoperative sternum and breast device that provides a constant lateral support on the sternum from the external side to complement the internal closure and which has means for increasing such external lateral sternum support to counteract the significantly increased internal thoracic pressure during various normal physical situations such coughing, sneezing, straining, breathing exercises etc. Furthermore there is a need for a postoperative sternum and breast device that can counteract the gravity forces caused by excessive obesity and breast tissue to prevent pulling on a wound, and particularly a sternal wound, as well as gently keep such sternal wound free of breast tissue. Furthermore there is a need for a postoperative sternum and breast device that in addition can provide access for wound care without the need to fully open such device and maintain women dignity during said wound care. Furthermore there is a significant need for a postoperative sternum and breast device that is comfortable to use day and night to assure that patients will comply with usage of such device in a period as long as 6-8 weeks until the wound and particularly a sternal wound is properly healed.

A surgical chest dressing is described in U.S. Pat. No. 6,135,975 to Johnstone which incorporates by reference U.S. Pat. No. 3,968,803 to Hyman; U.S. Pat. No. 5,152,741 to Farnio; and U.S. Pat. No. 5,538,502 to Johnstone. The described chest dressing is a brassiere directed towards improved support and comfort of the chest dressings and is "designed to improve support for a patient by holding the breasts of the patient relatively immobile while pressing them slightly toward the line of the incision". However, the surgical chest dressing described is squeezing a patient's side and breast tissue towards the center, whereby a wound in the thoracic area, and in particular a sternal wound, will be exposed to excessive pressure and heat-moist generation from the two breasts being pressed towards each other causing discomfort and pain for a woman with a fresh surgical wound, and in particular for obese and fuller-sized women. Such excessive pressure, heat-moist generation will result in increased potential for wound infections and other complications related to wound healing, as well as scar deformation. These are all complications that will lead to increased health care costs. Furthermore, there is no means for a continuous external support to the sternum in this device.

U.S. Pat. No. 4,804,351 to Rami et al. describes a surgical brassiere directed towards reducing stress along the mid-sternal incision line. The device has a pair of bust support cups and a ventilated panel over the gap between the cups. The ventilated panel can be opened for wound care and discloses how "a pair of inner straps, detachably secured across the gap between the bust support cups, assure that support continues to be provided while the ventilated panel is thus unsecured". However, while the brassiere may remain closed during wound care, there is no means to position the breast tissue to prevent gravitation to the sides, or to prevent the breast cups to squeeze the breast tissue towards the center. This will cause extra pulling stress and/or squeezing on a sternal wound and cause discomfort and pain for a patient, and in particular for obese patients and fuller-sized women. Such wound stress can result in increased infection and complication rates, which will lead to increased health care costs when treating such complications. Furthermore, there is no means for a continuous external support to the sternum in this invention.

U.S. Pat. No. 5,797,786 to Smith et al. describes a post-operative brassiere that has been "developed to provide a post-operative brassiere which completely eliminates the conventional torso straps that interconnect the bust support cups so as to form an exposed gap over the area of the patient's mid-sternal incision line to help promote healing and recovery". However, the brassiere has no means to stabilize the breast support cups and prevent gravitation to the sides or to prevent squeezing of the breast tissue towards the center. This will cause pulling stress and/or squeezing on a sternal wound and cause pain and discomfort for a fuller-sized woman, and in particular for obese patients. Such wound stress results in increased infection and complication rates, which will lead to increased health care costs when treating such complications. Furthermore, there is no means for a continuous external support to the sternum in this invention.

Sports bras and brassieres for athletic use generally aim at supporting and immobilizing the breasts to allow women to perform sports activities in a comfortable and painless way. Some of these brassieres are devoted to women with a large bust, such as U.S. Pat. No. 5,221,227 to Michels and U.S. Pat. No. 6,165,045 to Miller et al. Sports brassieres are sometimes employed to patients post-operatively for breast support. However, since they are designed for sports activities, they are generally not suitable for postoperative use and do not meet the specific needs both patients and health care personnel require after surgery. Furthermore, sports bras and brassieres have no means for a continuous external support to the sternum.

A brassiere for strenuous physical activity is described in U.S. Pat. No. 4,254,777 to Johnston and shows the use of "extra facings" around the bra cups to prevent undue movement of the breasts. These "facings" have no means to be adjusted and are too thin to give support or direct the position of a breast. Furthermore, there is no means for a continuous external support to the sternum in this invention.

A number of compression brassieres are available for use post-operatively for surgeries such as breast augmentation, reconstructive breast surgeries and other surgeries in the breast(s). Such compression brassieres have drawbacks and are not suitable for postoperative use after interventions inside the thorax, e.g. cardiothoracic surgery, since these devices are designed to compress the breast tissue with the aim to eliminate or reduce swelling caused by accumulation of lymph fluids after a surgical intervention in the breast(s), and/or to press downward newly inserted breast implants. A drawback for cardiothoracic patients using compression brassieres is that the breast tissue is compressed inwards, thereby squeezing and spreading the breast tissue over the thoracic wall in all directions. Such compression is very uncomfortable and painful and may cause healing complications for the wound, and in particular for a sternal wound, which will be exposed to undesirable high pressure and heat-moisture generation. This will increase the rate of wound infections and wound deformations. In particular, such undesirable high pressure on a sternal wound will increase the rate of wound complications in obese patients and for fuller-sized women. All postoperative complications lead to increased health care costs, when they need to be treated. Furthermore, these devices have no means for a continuous external support to the sternum.

Examples of prior art for a compression and post-partum breast engorgement bra are described in U.S. Pat. No. 5,839,942 to Miller and other compression devices are disclosed in U.S. Pat. No. 5,098,331 to Corrado; U.S. Pat. No. 5,037,348 to Farino; and U.S. Pat. No. 7,144,294 B2 to Bell et al.

A compression bra is described specifically for symmastia in U.S. Pat. No. 7,666,058 B2 to Smith. This design is directed towards a "compression stabilizing, supporting and positioning bra for addressing and/or correcting symmastia complications in reconstructive breast surgeries . . . " and has a "flared, trapezoidal shaped, sternum compression panel secured at its base to the upper edge of the torso band below the inframammary skinfold and at the top, by a pair of adjustable shoulder straps for elastically compressing sternum tissues while restraining shaping and separating the inside conically rising, side portions of a woman's breasts". While the device described obviously cannot be utilized for patients having had a sternotomy, it aims at "supporting and positioning" the breasts. However, there is no means to prevent gravitation of the breast tissue to the central or the lateral sides. Furthermore, the adjustable shoulder straps that are attached to a panel for elastically compressing the sternum tissue between a woman's breasts only pull a panel upwards and cannot support or direct a breast in any direction. There is no means for a continuous external support to the sternum in this invention.

In view of the foregoing, it is a general object of the present invention to provide a sternum and breast device that overcomes the problems of prior art devices and that can improve the postoperative care and experience for patients, decrease and prevent postoperative complications, and thereby decrease costs of health care in accordance with the features set forth in the claims that follow. The invention also includes a corresponding method.

SUMMARY OF THE INVENTION

The present invention relates to a sternum and breast device that provides a continuous adjustable, external lateral sternum support. The device may include a means to increase such support during coughing, sneezing and other situations where it is desirable to increase said support. The sternum and breast device provides individual support and positioning of the breasts for fuller-sized women and obese patients that have undergone surgeries requiring a sternotomy procedure. Various embodiments and optional features are disclosed herein. Distinguishing features that may be included in these embodiments are described below. It is intended that the embodiments described herein may include one or more of these features, individually or in combination, and it is not intended that this disclosure be limited to the specific combination of features described in connection with the embodiments or methods disclosed herein.

In one embodiment the invention includes a device for supporting the sternum and breasts of a patient after thoracic surgery. The device includes a chest encircling band of stretchable material having first and second ends, the chest encircling band being sized to extend around the chest of the patient above the breasts with the first end overlapping the second end along overlapping surfaces having a first adjustable attachment member to secure the chest encircling band about the patient's chest. The device further includes a first elongate band of stretchable material attached to the chest encircling band, the first elongate band having an under-bust portion defining a first end and a shoulder strap portion defining a second end, the first elongate band being sized to extend from under a first breast of the patient on a first side of the patient around the first side of the patient and upwards along the patient's back over the patient's shoulder on a second side of the patient opposite the first breast. The device further includes a second elongate band of stretchable material attached to the chest encircling band, the second elongate band having an under-bust portion defining a first end and a shoulder strap portion defining a second end, the second elongate band being sized to extend from under a second breast of the patient on a second side of the patient around the second side of the patient and upwards along the patient's back over the patient's shoulder on the first side of the patient opposite the second breast. The device also includes a first connection member connected to the shoulder strap portion of the second elongate band and a second connection member connected to the shoulder strap portion of the first elongate band. A first breast encapsulating unit has a lower portion attached to the under-bust portion of the first elongate band and an upper portion attached to the first connection member and a second breast encapsulating unit has a lower portion attached to the under-bust portion of the second elongate band and an upper portion attached to the second connection member. The first end of the first elongate band overlaps the first end of the second elongate band along overlapping surfaces having a second adjustable attachment member to secure the first and second elongate bands about the patient's chest under the patient's breasts. Also disclosed herein are certain additional features and structure that might be included in the supporting device including the following.

The first breast encapsulating unit may comprise a first central vertical band, a first lateral vertical band and a first breast cup connected between the first central vertical band and the first lateral vertical band, and the second breast encapsulating unit may comprise a second central vertical band, a second lateral vertical band and a second breast cup connected between the second central vertical band and the second lateral vertical band.

The supporting device may further include one or more middle adjustment bands. For example, the supporting device may include a first adjustment band having a first end and a second end, the first end attached to the first breast encapsulating unit, the first adjustment band further having means for adjustably connecting the second end of the first adjustment band to one of the second breast encapsulating unit, the second connection member and the shoulder strap portion of the first elongate band. Additionally, the supporting device may comprise a second adjustment band having a first end and a second end, the first end attached to the second breast encapsulating unit, the second adjustment band further having means for adjustably connecting the second end of the second adjustment band to one of the first breast encapsulating unit, the first connection member and the shoulder strap portion of the second elongate band. One or more additional adjustment bands may be provided to extend from the first breast encapsulating unit and/or the second breast encapsulating unit.

The first connection member may define first and second elongate slits, and the second connection member may define first and second elongate slits. The second end of the second elongate band is sized to be received in the first elongate slit of the first connection member. In that embodiment the second elongate band includes means for adjustably connecting the second elongate band to the first connection member. Further, an upper free end of the first central vertical band is sized to be received in the second elongate slit of the first connection member and the first central vertical band includes means for adjustably connecting the first central vertical band to the first connection member. The second end of the first elongate band is sized to be received in the first elongate slit of the second connection member and the first elongate band includes means for adjustably connecting the first elongate band to the second connection member. An upper free end of the second central vertical band is sized to be received in the second elongate slit of the second connection member and the second central vertical band includes means for adjustably connecting the second central vertical band to the second connection member. Still further, the first connection member may define a third elongate slit, and the second connection member may define a third elongate slit. An upper free end of the first lateral vertical band is sized to be received in the third elongate slit of the first connection member and the first lateral vertical band includes means for adjustably connecting the first lateral vertical band to the first connection member. An upper free end of the second lateral vertical band is sized to be received in the third elongate slit of the second connection member and the second lateral vertical band includes means for adjustably connecting the second lateral vertical band to the second connection member.

The first and second elongate slits of the first connection member are oriented 90° with respect to the third elongate slit of the first connection member and the first and second elongate slits of the second connection member are oriented 90° with respect to the third elongate slit of the second connection member.

Further, the first and second adjustable attachment members may comprise one of a hook and loop fastener, buckle, zipper, snap, laces, and buttons.

The first elongate band may be attached to the chest band by first, second and third vertically oriented lines of stitches, the first line being longer than the second and third lines and being positioned closer to the first end of the first elongate band than the second and third lines. Additionally, the second elongate band may be attached to the chest band by first, second and third vertically oriented lines of stitches, the first line being longer than the second and third lines and being positioned closer to the first end of the second elongate band than the second and third lines.

BRIEF DESCRIPTION OF THE DRAWINGS

A form of the present invention will now be described by way of non-limiting example with reference to the accompanying drawings, wherein.

DETAILED DESCRIPTION OF EMBODIMENTS

The present invention provides for a sternum and breast device that applies a continuous adjustable lateral support to the sternum from the external side. The device may include means to allow the patient to increase such support as necessary. Further, the device includes breast supports with means to adjust the position of the breasts individually to keep the breast tissue away from the mid-center of the chest to avoid heat and moisture generation, as well as to prevent gravitation of the breast tissue to the lateral sides of the thoracic cavity. The sternum and breast device of the present invention is designed to prevent postoperative complications by providing a continuous external lateral support on the sternum, by promoting better coughing and breathing exercises, by decreasing pain and wound complications, and by reducing heat and moisture production between the breast tissue. The sternum and breast device of the present invention is furthermore designed to improve wound access for safe inspection and care, to decrease pain by maintaining breast support, to preserve dignity during wound care, and to improve wound healing for a more esthetically pleasing appearance. The sternum and breast device of the present invention is furthermore designed to be comfortable, soft, light and perspiration absorbing, and allowing patients comfortably to sleep with the device and wear it long term.

Figure 1:
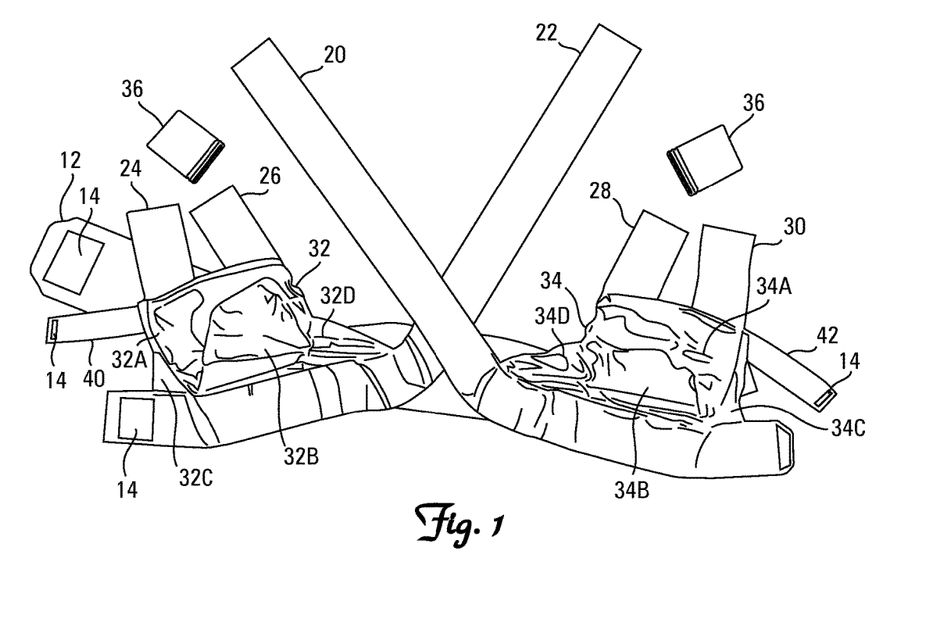
FIG. 1 is front view of the sternum and breast device of the present invention laid out flat and disassembled to show the interior surface of the device which is against the skin of the patient when the device is in use.
Figure 2:
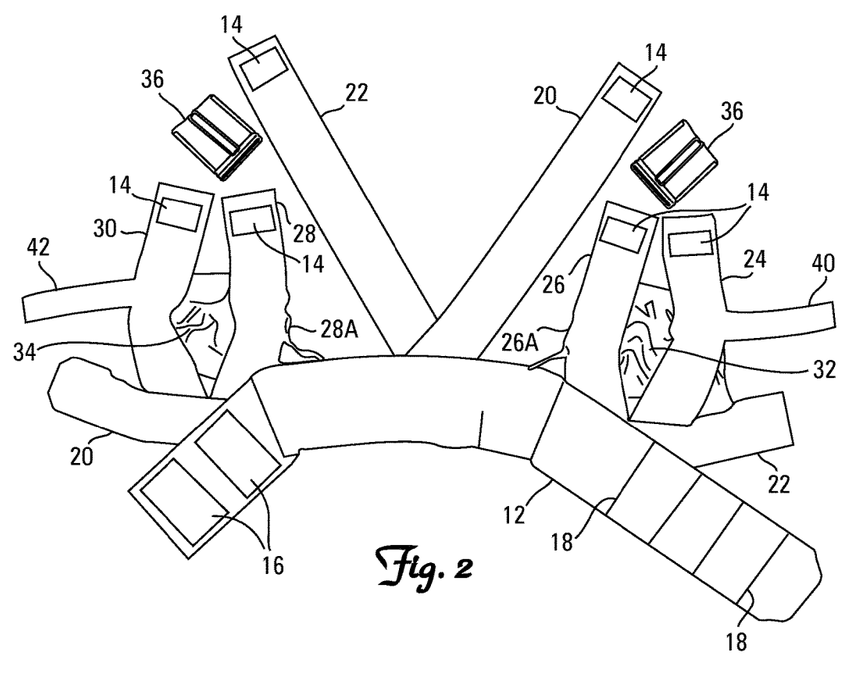
FIG. 2 is back view of the sternum and breast device of the present invention laid out flat and disassembled to show the exterior surface of the device when the device is in use.

FIGS. 1 and 2 are front and back views, respectively, of the sternum and breast device 10 of the present invention laid out flat and disassembled. Device 10 includes a chest band 12 which forms a circle around a patient's chest that passes above the breasts at front, under the armpits and at the middle back as will be described in more detail hereafter. Device 10 also includes first and second elongate underbust/shoulder bands 20 and 22. Device 10 further includes a first breast encapsulating unit that may comprise breast cup 32 and vertical bands 24 and 26, and a second breast encapsulating unit that may comprise breast cup 34 and vertical bands 28 and 30. Two coupling connectors 36 are provided to allow for attachment of bands 20, 24 and 26, and for attachment of bands 22, 28 and 30, as will be described in more detail hereafter. Breast cups 32 and 34 are sized, shaped and constructed as desired to receive breast tissue. The device 10 may also include two middle adjustment bands 40 and 42 which allow for individual adjustment of the breast cups as described in more detail hereafter. Optionally, two additional middle adjustment bands may be provided if additional control of the breast encapsulating units is desired.

In one embodiment each breast cup has an upper part (32A, 34A) and a lower part (32B, 34B) that when sewn together forms a bowl to encapsulate a breast. The lower half circle part (32B, 34B) of each breast cup is attached to an under-cup part made of the same material as the breast cup and formed as a half circle with central (32C, 34C) and lateral (32D, 34D) side parts that rest against a patient's chest when the breast cup encapsulates a breast. Both the breast cups and under-cups are made double and placed wrong-side against wrong-side so all seams are hidden whereby there is no seams to cause any irritation. The material of the breast cup and under-cup part may be made of any flexible material, for example, a mix of cotton and elastomers is used to add flexibility for encapsulating several breast sizes. In one embodiment the material is made of 10% latex-free elastomer and 90% cotton for comfort and absorption of perspiration. The use of flexible elastic material enables the breast cup to encapsulate several breast sizes.

Figure 3:
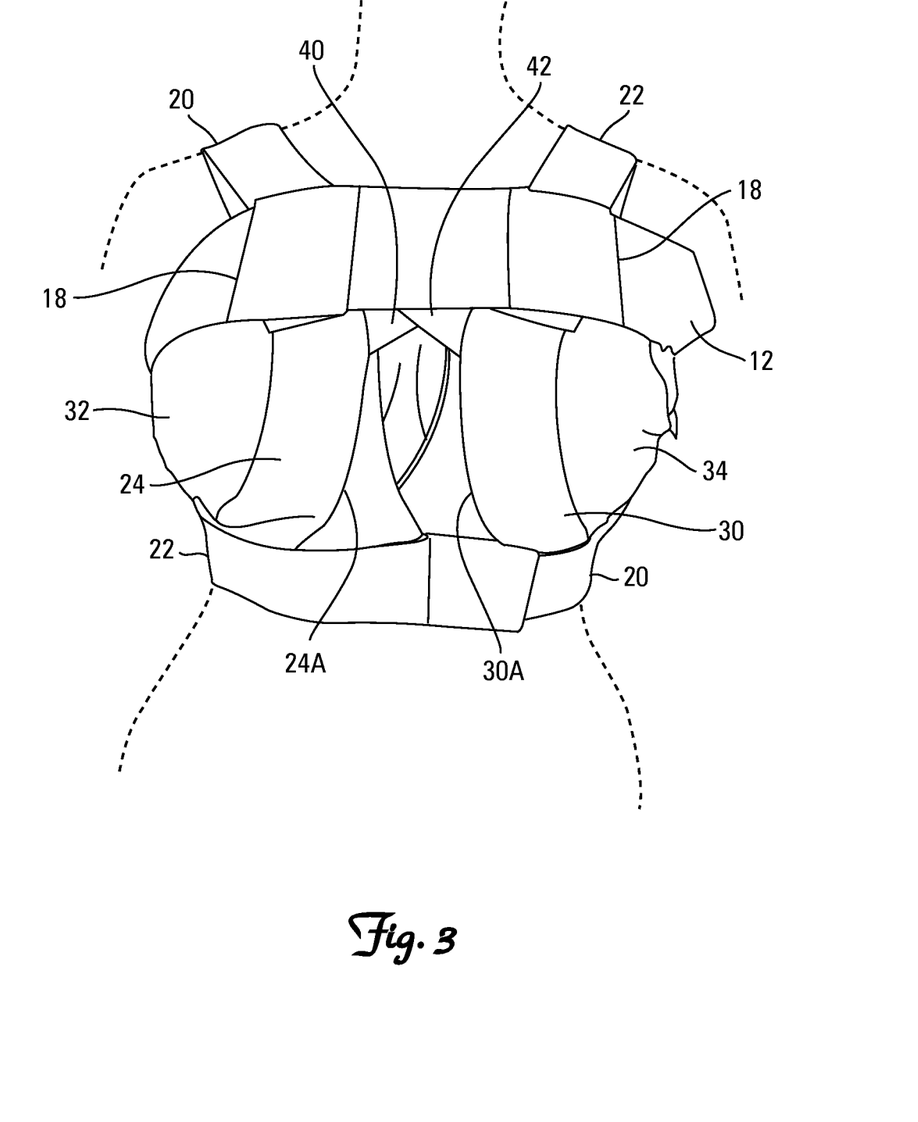
FIG. 3 is a front view of the supporting device assembled and worn by a patient.

The chest band 12 may be closed at any point along the band. For example, as best seen in FIG. 3, which is a front view of the device assembled and worn by a patient, it may be closed at the front left side of the patient. The chest band 12 may be provided with an adjustable closing means such as fabric hook fastener 14 attached at a first end and fabric loop fasteners 16 attached at a second end, but it may be closed using other means such as buckles, zipper, strings or laces, buttons, snaps and the like to form an adjustable closure. As shown in FIG. 3, the chest band 12 is closed on the left side of the patient by attaching the fabric hook fastener 14 at the first end to one of the fabric loop fasteners 16 at the second end. The chest band 12 may be provided with pressure adjustment means to allow the patient to increase the pressure applied by band 12, as desired. For example, the pressure adjustment means may comprise two pouches 18 formed by the band material and positioned on each side from the central front part of the chest. The purpose of the pouches 18 is to give means to the patient to increase the surrounding support on the chest as needed and to counteract increased internal chest pressures. To use the pouches 18, the patient inserts her left thumb or 4 digits into the pouch on the left side of the sternum, and she inserts her right thumb or 4 digits into the pouch on the right side of the sternum. When she brings her thumbs or digits together or on top of each other over the sternum, the pouches will stretch the circular band material to provide additional chest encircling support from the band, which is especially useful during a cough, sneeze, or strain and for managing breathing and pain. The pouches 18 preferably may be integrated in the material as here described, or they may be externally attached to the band material and made of any suitable material to accommodate a patient's thumbs or digits. Alternatively, the pressure adjustment means may comprise handles or tabs which are positioned to be grasped by the patient and move toward one another to increase the pressure applied by band 12. The chest band 12 material may be made of any flexible material and have a width from 3 cm. to 25 cm. For example, the chest band 12 may be made of precisely defined stretchable, ventilated, latex-free material and have a width of 10 cm.

Figure 4:
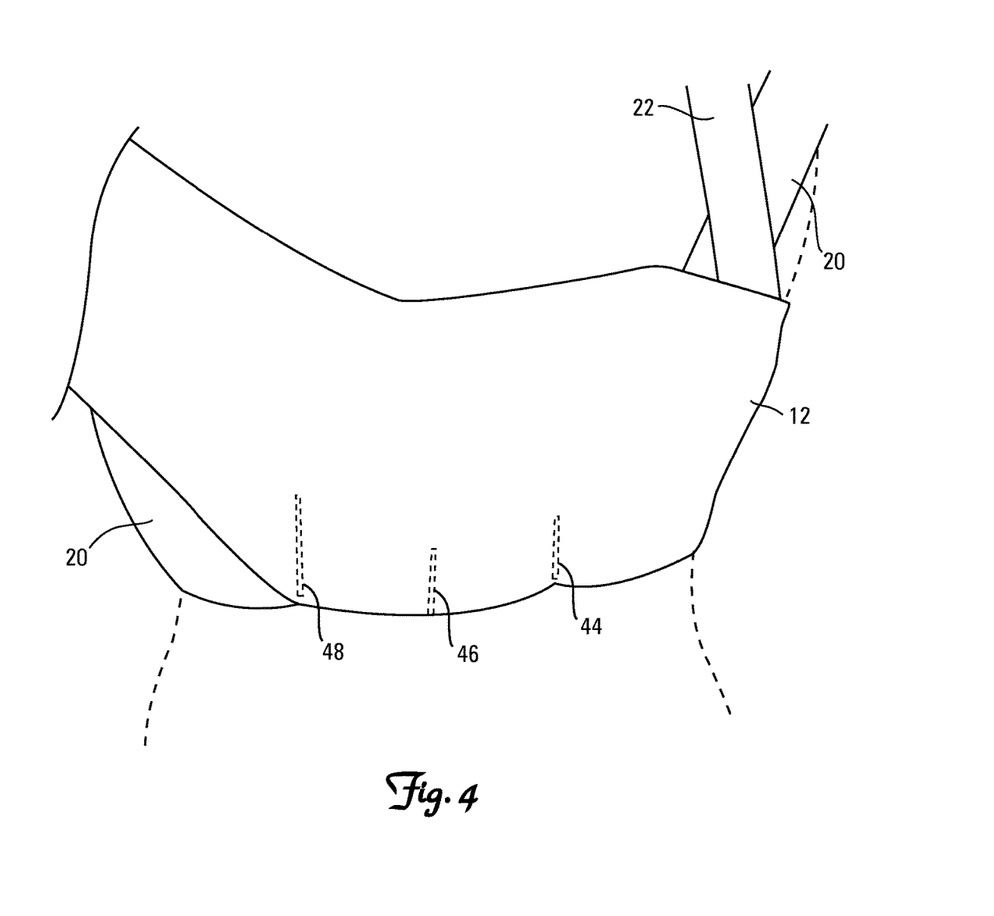
FIG. 4 is a partial back side perspective view of the supporting device worn by a patient.

Under-bust/shoulder bands 20 and 22 may be made of any elastic material. Each band 20 and 22 comprises an under-bust portion and a shoulder strap portion. Preferably they are made of latex-free elastic loop fabric material. The width of the under-bust/shoulder bands may be between 2 cm to 10 cm. In one embodiment the width is 6 cm. One end of the under-bust portion of first under-bust/shoulder band 20 is positioned horizontally underneath the first breast. Band 20 is then directed around the patient's side towards the back and attached to the chest band 12 under the armpit by any conventional means of attachment such as adhesives, stitches and the like. For example, the attachment may be made by three vertically oriented lines of stitches 44, 46 and 48 of different lengths as best seen in FIG. 4 which is a back side perspective view of the device 10 worn by a patient. Of course, more or fewer lines of stitches, oriented as desired, could be used. Stitches 44, 46 and 48 are positioned to generally align a bottom edge of band 20 with a bottom edge of chest band 12 along an attachment area which is the distance between stitches 44 and 48. This functionally integrates the chest band 12 with band 20 in the attachment area. Stitch line 48 is longer than stitch lines 44 and 46 and may have a length which is equal to or nearly equal to the width of band 20. The longer length of stitch line 48 ensures a proper integration and alignment of chest band 12 and elongate band 20. Additionally, stitch 48 effectively maintains the chest band 12 at a lower position around the patient's chest so that the patient's armpits remain free of the chest band 12. Stitch 48 is positioned closer to the first end of elongate band 20 than stitches 44 and 46. Stitches 44 and 46 are located nearer the midline of the patient's back and are shorter in order to provide for a smooth transitional upward release of the shoulder strap portion of elongate band 20 so that it more easily conforms to the upwards curve across the patient's back and over the patient's shoulder. After this attachment the shoulder strap portion of the under-bust/shoulder band 20 continues upwards at the back crossing over to the opposite side and over the first shoulder of the patient. One end of the under-bust portion of the second under-bust/shoulder band 22 is positioned horizontally underneath the second breast. Band 22 is then directed towards the back and attached to the chest band in a manner similar to that described with respect to band 20. One of the under-bust/shoulder bands, for example band 22, has a hook fabric fastener 14 attached at the under-bust portion end (FIG. 1) as well as the shoulder strap portion end (FIG. 2). The second under-bust/shoulder band, for example band 20, only has hook fabric attached at the shoulder part end (FIG. 2). The under-bust portion end part of band 20 comprises loop material. All the four ends of the under-bust/shoulder bands are folded and stitched to make it easy to take a hold of the band material when positioning the device on a patient. The hook fabric at the under-bust portion end part of band 22 enables attaching the two under-bust/shoulder bands together at the patients mid front underneath the breasts when the hook fabric fastener is placed onto the overlapping opposite side elastic loop material of the under-bust portion end part of band 20.

Breast cups 32 and 34 are attached between the vertical bands in the following manner. As best seen in FIG. 3, one end of vertical band 24 is attached centrally under breast cup 32 and one end of vertical band 30 is attached centrally under breast cup 34. The central side edge 24A of band 24 is vertically attached to the central side edge of breast cup 32. The central side edge 30A of band 30 is vertically attached to the central side edge of breast cup 32. As best seen in FIGS. 1 and 2, one end of vertical band 28 is attached centrally under breast cup 34 to band 20 and one end of vertical band 26 is attached centrally under breast cup 32 to band 22. A lateral side edge 28A of band 28 is attached to a lateral side edge of breast cup 34 and a lateral side edge 26A of band 26 is attached to a lateral side edge of breast cup 32. The upper part of each of the vertical bands are unattached to the breast cups. For example, up to 50% of the four bands are unattached to the breast cups which will aid flexibility for adjusting the breast position both on the central and lateral sides. The bands may be made of any elastic material, preferably the bands are made of latex-free elastic loop fabric material. Each of the four vertical bands 24, 26, 28 and 30 have a piece of hook fabric 14 attached at the end of the unattached part of the bands. A substantial portion of the remaining exposed material of the bands is comprised of loop material to enable the hook fabric to be attached in any desired position. All the four ends of the vertical bands are folded and stitched to make it easy to take a hold of the band material.

Breast cup 32 together with under cup parts 32C, 32D and vertical bands 24 and 26 are attached to a top edge of the under-bust/shoulder band 22, leaving an end of the under-bust band 22 free for facilitating the front closure. Breast cup 34 together with under cup parts 34C, 34D and vertical bands 28 and 30 are attached to a top edge of the under-bust/shoulder band 20, leaving an end of the under-bust band 20 free for facilitating the front closure. As previously described, the front closure is by means of hook and loop fabric, but may be with any other closure means such as buckles, hook and loop devices, strings or the like.

Figure 5:
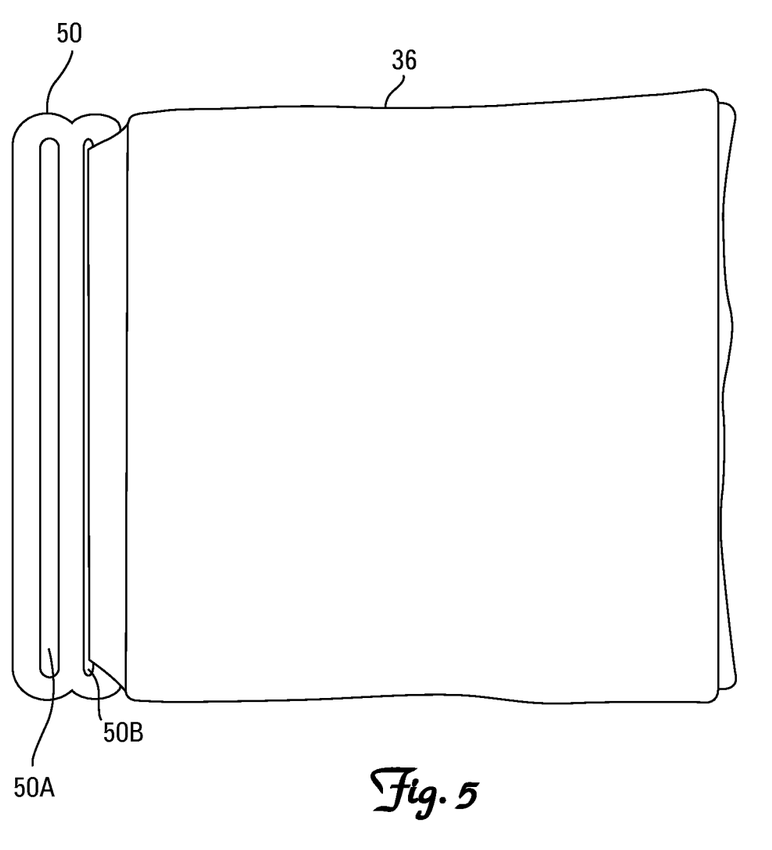
FIGS. 5 and 6 are enlarged plan views of the interior and exterior surfaces of a coupling connector.
Figure 6:
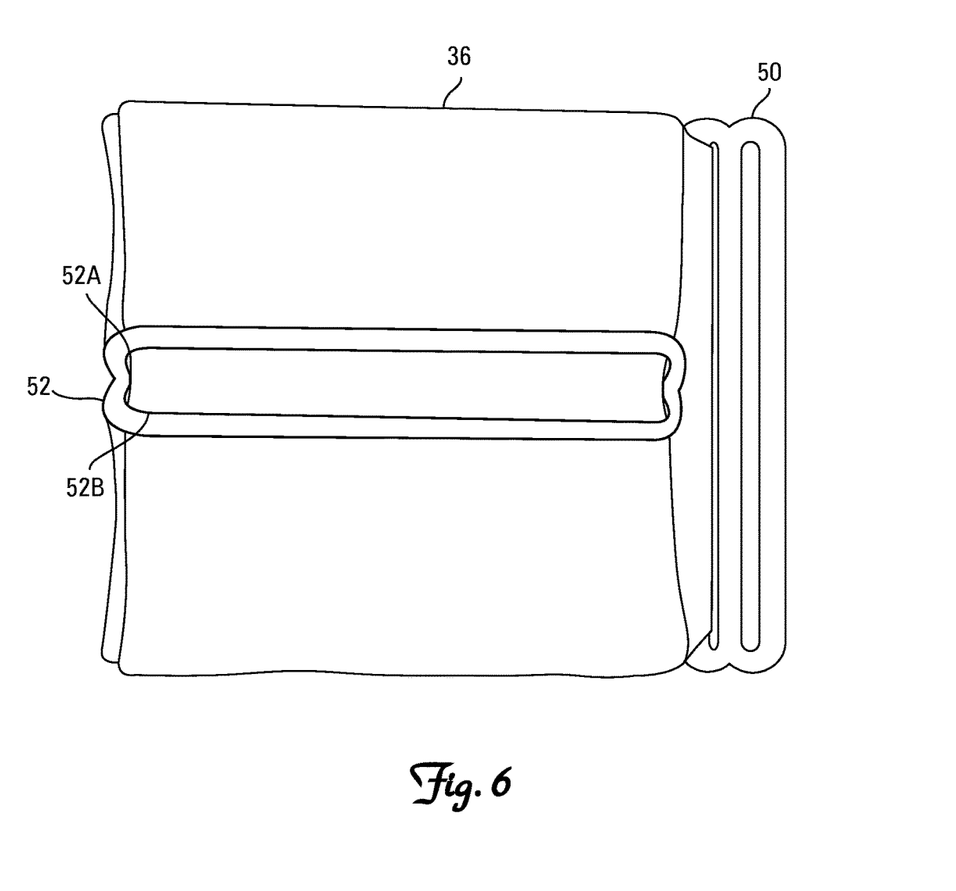

Two coupling connectors 36 are used to attach the shoulder strap portion of bands 20 and 22 with upper portions of the breast encapsulating units. For example, coupling connectors 36 are used to attach the shoulder strap portion of under-bust/shoulder band 20 with the unattached end of the central-vertical band 24 of the breast cup 32, and the shoulder strap portion of under-bust/shoulder band 22 with the unattached end of the central-vertical band 30 of the breast cup 34. Coupling connectors 36 may be identical in structure and differ in device 10 only in the direction in which they are oriented. Alternatively, coupling connectors 36 may comprise a right hand connector and a left hand connector as described more fully below. The structure of the connectors is shown in FIGS. 5 and 6 which are enlarged plan views of the inner and outer surfaces of connector 36. The inner surface is that surface that is placed against the body of the patient and the outer surface is that surface that is oriented away from the patient's body. Each coupling connector includes a fabric portion and two adjusters 50 and 52 which are attached to the fabric portion. Adjuster 50 is mounted to one side of the connector. Adjuster 52 is mounted centrally on the outer surface of the connector and oriented at a 90 degree angle with respect to adjuster 50. Adjuster 50 has slit openings 50A and 50B and adjuster 52 has slit openings 52A and 52B. The fabric material of the fabric portion of connector 36 extends through slit 50B to attach adjuster 50 to connector 36. Fabric material generally extends through both slits 52A and 52B to retain attach adjuster 52 at a central location on the fabric portion of connector 36. The size and shape of the adjusters may be identical. The slit openings may be the same or different width/diameters. In one embodiment where right and left hand versions of connector 36 are used, the upper slit (during use) of adjuster 52, which receives the shoulder strap portion, is wider than the lower slit. For example, the lower slit may have a 3 mm diameter (width) and the upper slit a 6 mm diameter (width). The wider opening in the upper slit of adjuster 36 as it is positioned during use allows for ease of insertion of the shoulder strap portion during use, as described below. The coupling connectors may be made of latex-free elastic loop fabric material, but may be made of any suitable material, elastic or non-elastic. The adjusters preferably are made of stainless steel coated with nylon powder and have the same width as the bands, but may be made of any material strong enough to withstand the pulling forces.

The shoulder strap portion end of band 20 is attached to the unattached end of central vertical band 24 by inserting the end of band 20 into slit 52B and the end of band 24 into slit 52A of adjuster 52. This results in a continuing line of the central-vertical band 24 and the shoulder strap portion of band 20 interrupted only by the adjuster. The tension of each band 20 and 24 is individually adjustable by varying the position at which the hoop fastener is attached to loop material forming the outer surface of the bands. Optionally, other attachment means as described herein may be used. Such central-vertical band/shoulder band line will assist to keep the breast tissue encapsulated in the breast cups and away from the center of the chest. The unattached end of lateral-vertical band 26 is attached by inserting the free end through slit 50A of adjuster 50 to allow for control of the breast position in relation to the potential lateral pulling force caused by heavy breast tissue. The tension of band 26 is individually adjustable by varying the position at which the hoop fastener is attached to loop material forming the outer surface of the band. In a similar manner, the shoulder strap end of band 22 is attached to the unattached end of central vertical band 30 by inserting the end of band 22 into slit 52A and the end of band 30 into slit 52B of adjuster 52. This results in a continuing line of the central-vertical band 30 and the shoulder strap portion of band 22 interrupted only by the adjuster. The unattached end of lateral-vertical band 28 is attached by inserting the free end through slit 50A of adjuster 50 to allow for control of the breast position in relation to the potential lateral pulling force caused by heavy breast tissue.

The two coupling connectors above each breast cup allow for tension-adjustments of the central-vertical bands 24, and 28 as well as the shoulder band portions of the under-bust/shoulder bands 20 and 22 in a continuing line, whereby the breasts can be positioned in the most favorable way to keep the central part of the chest free of breast tissue to avoid moist and heat generation in that area, and by adjusting the shoulder strap part of the under-bust/shoulder band, the best position of the breast cups can be achieved in respect to a horizontal level. Furthermore the two coupling connectors make it possible to tension-adjust the lateral-vertical bands on each side of the breasts to get the best support to the breast tissue to avoid pulling in the lateral direction caused by the weight of breast tissue.

Figure 7:
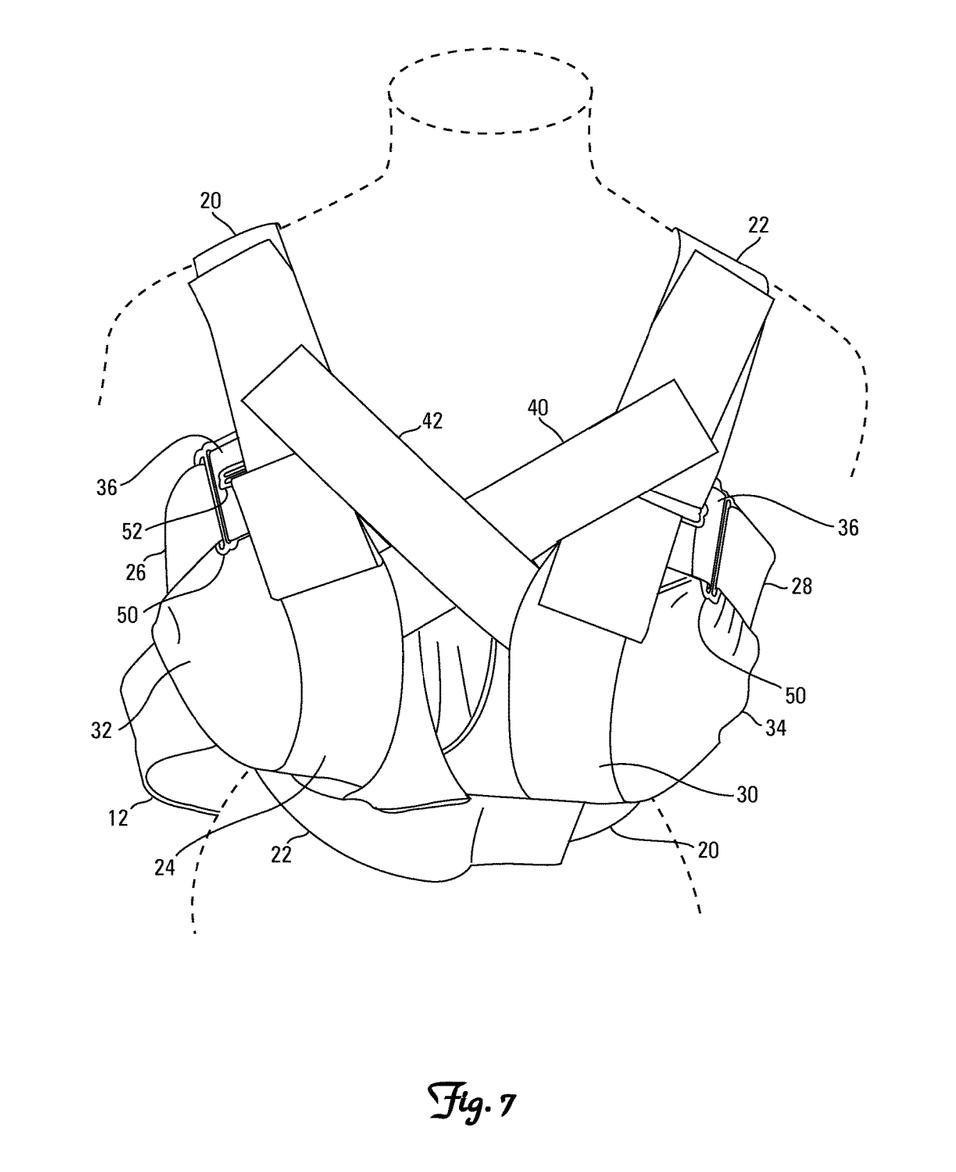
FIGS. 7 and 8 are front views of the supporting device worn by a patient with the chest band disconnected and pulled back to show two examples of the position and/or configuration in which the middle adjustment bands may be attached.
Figure 8:
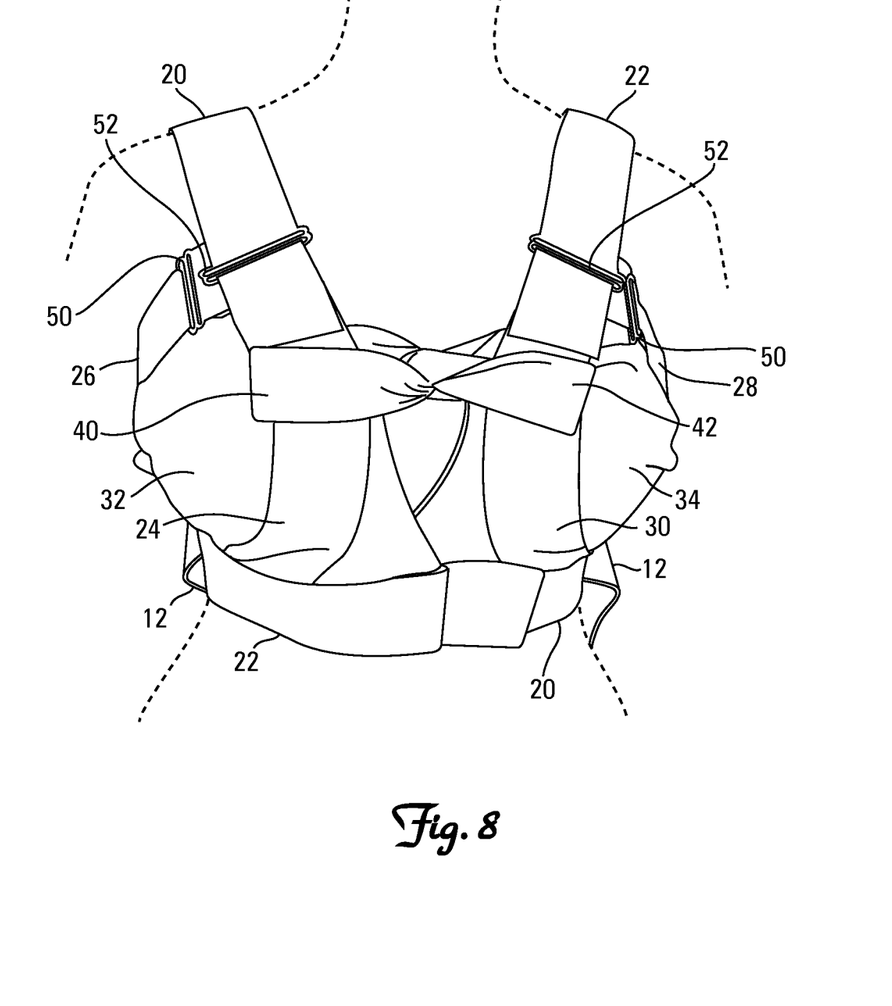

A first end of middle adjustment band 40 is fixedly attached between breast cup 32 and central vertical band 24 and a first end of middle adjustment band 42 is fixedly attached between breast cup 34 and central vertical band 30. The second free end of each middle adjustment band is equipped with a hook fabric fastener 14. Preferably, a substantial portion of the outer exposed surface of central-vertical bands 24 and 30 and under-bust/shoulder bands 20 and 22 comprises an elastic loop material which enables each middle adjustment band to be attached to the central-vertical bands or the shoulder strap portions of the elongate bands of the opposite breast cup at any point. FIGS. 7 and 8 show two examples of the position and/or configuration in which the middle adjustment bands may be attached. FIG. 7 shows the free end of middle adjustment band 40 connected to band 22 coupling above connector 36 and the free end of middle adjustment band 42 connected to band 20 above connector 36. In FIG. 8 middle adjustment bands 40 and 42 are looped about each other at the center so that the free ends return to attach at or near the other ends of each band below the coupling connectors. There are many alternative ways in which the free ends of the middle adjustment bands can be attached or fixed. For example, the free ends can be attached at any position along either central-vertical bands 24 and 30 or the shoulder strap portions of bands 20 and 22. Further, if the free ends of the middle adjustment bands are attached prior to attachment of bands 24 and 30 or 20 and 22 the free ends of those bands can be connected over the free ends of the middle attachment bands. The two middle adjustment bands allow for additional and individual adjustment of the breasts in relation to the central chest area. Furthermore, each middle adjustment band allows for flattening out of any skin fold caused by the breast tissue. The bands may be made of any elastic or non-elastic material, for example, they may be made of latex-free elastic loop fabric material, and may have a width between 0.2 cm and 6 cm. For example, in one embodiment the width is 2 cm.

The sternum and breast device of the present invention provides an open central area between the two breast cups, the under-bust band and the middle adjustment bands which allows inspection of a sternal wound without the need to open the device.

The sternum and breast device of the present invention provides support to the breasts at all times with or without the attachments of the middle adjustment bands to the opposite central-vertical bands due to the straight alignment of the central-vertical bands with the shoulder-straps part of the under-bust/shoulder bands that keeps the breast tissue away from the center of the chest, and which eliminates the need to open the under-bust band closure during wound care, as well as it preserves dignity by keeping the breast tissue covered which is particularly of importance for patients of different ethnic origins.

The sternum and breast device of the present invention provides for easy and simplified sizing where the chest band is the determining factor instead of the bra cup as in the invention of U.S. Pat. No. 8,932,103 B2 to Hansen. The chest band is the determining factor for sizing due to the integration of the chest band with the under-bust/shoulder band by the 3 side stitches on each side of a patient's torso whereby the under-bust band at the patient's front continues around the back to become the chest band, which makes the under-bust part appear as in a normal brassiere. In contrast to a normal under-bust band the sternum and breast device of the present invention provides a back side of the under-bust band which is the adjustable chest band, and since the breast cup material is flexible and elastic, which makes the breast cups able to encapsulate all standard breast sizes, the chest band becomes the determining factor for sizing of the sternum and breast device. The sternum and breast device of the present invention therefore provides for a sizing method simplified by measuring the circumference of patient's chest above the breast at the chest band position, which results in few stock items needed of the device.

The sternum and breast device of the present invention provides comfort to the patients due to combination of the soft, flexible, absorbable and light material used which encourages patient's to use it, to sleep with it and ensure protection of their sternum for up to 6-8 weeks until proper healing has taken place.

What is claimed is:

1. A device for supporting the sternum and breasts of a patient after thoracic surgery comprising:
   a chest encircling band of stretchable material having first and second ends, the chest encircling band being configured and sized to extend around the chest of the patient above the breasts with the first end overlapping the second end along overlapping surfaces having a first adjustable attachment member configured to secure the chest encircling band about the patient's chest;
   a first elongate band of stretchable material attached to the chest encircling band, the first elongate band having an under-bust portion defining a first end and a shoulder strap portion defining a second end, the first elongate band being configured and sized to extend from under a first breast of the patient on a first side of the patient around the first side of the patient and upwards along the patient's back over the patient's shoulder on a second side of the patient opposite the first breast;
   a second elongate band of stretchable material attached to the chest encircling band, the second elongate band having an under-bust portion defining a first end and a shoulder strap portion defining a second end, the second elongate band being configured and sized to extend from under a second breast of the patient on a second side of the patient around the second side of the patient and upwards along the patient's back over the patient's shoulder on the first side of the patient opposite the second breast;
   a first connection member connected to the shoulder strap portion of the second elongate band;
   a second connection member connected to the shoulder strap portion of the first elongate band;
   a first breast encapsulating unit having a lower portion attached to the under-bust portion of the first elongate band and an upper portion attached to the first connection member;
   a second breast encapsulating unit having a lower portion attached to the under-bust portion of the second elongate band and an upper portion attached to the second connection member; and
   the first end of the first elongate band overlapping the first end of the second elongate band along overlapping surfaces having a second adjustable attachment member configured to secure the first and second elongate bands about the patient's chest under the patient's breasts.

2. The supporting device of claim 1 wherein the first breast encapsulating unit comprises a first central vertical band, a first lateral vertical band and a first breast cup connected between the first central vertical band and the first lateral vertical band, and wherein the second breast encapsulating unit comprises a second central vertical band, a second lateral vertical band and a second breast cup connected between the second central vertical band and the second lateral vertical band.

3. The supporting device of claim 1 further comprising a first adjustment band having a first end and a second end, the first end attached to the first breast encapsulating unit, the first adjustment band further having means for adjustably connecting the second end of the first adjustment band to one of the second breast encapsulating unit, the second connection member and the shoulder strap portion of the first elongate band.

4. The supporting device of claim 3 further comprising a second adjustment band having a first end and a second end, the first end attached to the second breast encapsulating unit, the second adjustment band further having means for adjustably connecting the second end of the second adjustment band to one of the first breast encapsulating unit, the first connection member and the shoulder strap portion of the second elongate band.

5. The supporting device of claim 1 wherein the first connection member comprises a fabric portion and a first adjuster attached to the fabric portion, the first adjuster of the first connection member defining first and second elongate slits, and wherein the second connection member comprises a fabric portion and a first adjuster attached to the fabric portion, the first adjuster of the second connection member defining first and second elongate slits, the second end of the second elongate band being configured and sized to be received in the first elongate slit of the first connection member, the second elongate band including means for adjustably connecting the second elongate band to the first connection member, an upper free end of the first central vertical band being configured and sized to be received in the second elongate slit of the first connection member, the first central vertical band including means for adjustably connecting the first central vertical band to the first connection member, the second end of the first elongate band being configured and sized to be received in the first elongate slit of the second connection member, the first elongate band including means for adjustably connecting the first elongate band to the second connection member, an upper free end of the second central vertical band being configured and sized to be received in the second elongate slit of the second connection member, the second central vertical band including means for adjustably connecting the second central vertical band to the second connection member.

6. The supporting device of claim 5 wherein the first connection member comprises a second adjuster attached to the fabric portion of the first connection member, the second adjuster of the first connection member defining a third elongate slit, and wherein the second connection member comprises a second adjuster connected to the fabric portion of the second connection member, the second adjuster of the second connection member defining a third elongate slit, an upper free end of the first lateral vertical band being configured and sized to be received in the third elongate slit of the first connection member, the first lateral vertical band including means for adjustably connecting the first lateral vertical band to the first connection member, an upper free end of the second lateral vertical band being configured and sized to be received in the third elongate slit of the second connection member, the second lateral vertical band including means for adjustably connecting the second lateral vertical band to the second connection member.

7. The supporting device of claim 6 wherein the first and second elongate slits of the first connection member are oriented 90° with respect to the third elongate slit of the first connection member and wherein the first and second elongate slits of the second connection member are oriented 90° with respect to the third elongate slit of the second connection member.

8. The supporting device of claim 5 wherein the first elongate slit of the first connection member is wider than the second elongate slit of the first connection member and wherein the first elongate slit of the second connection member is wider that the second elongate slit of the second connection member.

9. The supporting device of claim 1 wherein the first adjustable attachment member comprises one of a hook and loop fastener, buckle, zipper, snap, laces, and buttons.

10. The supporting device of claim 1 wherein the second adjustable attachment member comprises one of a hook and loop fastener, buckle, zipper, snap, laces, and buttons.

11. The supporting device of claim 1 wherein the first elongate band is attached to the chest band by first, second and third vertically oriented lines of stitches, the first line being longer than the second and third lines and being positioned closer to the first end of the first elongate band than the second and third lines, and wherein the second elongate band is attached to the chest band by first, second and third vertically oriented lines of stitches, the first line being longer than the second and third lines and being positioned closer to the first end of the second elongate band than the second and third lines.

12. The supporting device of claim 1 wherein the chest band comprises means for adjusting the pressure applied to the patient's chest by the chest band.

* * * * *